United States Patent [19]
Nelson

[11] 4,099,013
[45] Jul. 4, 1978

[54] 4,5,6-TRINOR-3,7-INTER-M-PHENYLENE PROSTAGLANDIN $E_1$ ANALOGS

[75] Inventor: Norman A. Nelson, Galesburg, Mich.

[73] Assignee: The Upjohn Company, Kalamazoo, Mich.

[21] Appl. No.: 764,331

[22] Filed: Jan. 31, 1977

Related U.S. Application Data

[63] Continuation-in-part of Ser. No. 691,398, Jun. 1, 1976, abandoned, which is a continuation-in-part of Ser. No. 604,158, Aug. 13, 1975, abandoned.

[51] Int. Cl.$^2$ ............................................. C07C 69/76
[52] U.S. Cl. .................................. 560/53; 260/520 R
[58] Field of Search ........................ 560/53; 260/520 R

[56] References Cited
PUBLICATIONS

Derwent Abst., 09170X/05, U.S. 3933-899, 20-01-76.
Derwent Abst., 09171X/05, U.S. 3933-900, 25-01-76.
Derwent Abst., 09169X/05, U.S. 3933-898, 20-01-76.
Derwent Abst., 09166X/05, U.S. 3933-895, 20-01-76.

*Primary Examiner*—Paul J. Killos
*Attorney, Agent, or Firm*—Morris L. Nielsen

[57] ABSTRACT

This invention is a group of 4,5,6-trinor-3,7-inter-m-phenylene prostaglandin-type compounds and processes for making them. These compounds are useful for a variety of pharmacological purposes, including hypotensive control and inhibition of platelet aggregation.

A typical formula for a $PGE_1$-type analog is:

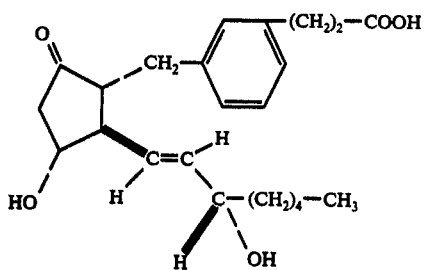

89 Claims, No Drawings

4,5,6-TRINOR-3,7-INTER-M-PHENYLENE PROSTAGLANDIN E₁ ANALOGS

CROSS REFERENCE TO RELATED APPLICATIONS

This application is a continuation-in-part of co-pending application Ser. No. 691,398 filed Jun. 1, 1976, now abandoned which is a continuation-in-part of then co-pending application Ser. No. 604,158 filed Aug. 13, 1975, and since abandoned.

BACKGROUND OF THE INVENTION

This invention relates to compositions of matter, and to methods and intermediates for producing them. In particular, the several aspects of this invention relates to novel phenylene analogs of some of the known prostaglandins, i.e. prostaglandin $E_1$ ($PGE_1$), prostaglandin $F_1\alpha$ ($PGF_1\alpha$), and prostaglandin $A_1$ ($PGA_1$).

The essential material for this application, including the background of the invention, the disclosure of the invention, and the description of the preferred embodiments, including Preparations and Examples, is incorporated by reference from pending and commonly owned allowed U.S. application Ser. No. 764,333 filed Jan. 31, 1977, for which the issue fee has been paid, now issued as U.S. Pat. No. 4,084,058 under the provisions of M.P.E.P. 608.01(p).

Previously, certain phenylene-containing prostaglandin analogs were disclosed. See U.S. Pat. Nos. 3,933,897, 3,933,898, and 3,944,595, for a group of phenyleneoxa compounds having a divalent phenylene moiety

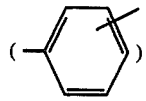

and an oxa oxygen (-O-) in the carboxyl-terminated side chain. See Belgian Pat. No. 820,003, Derwent Farmdoc 22475W for related compounds which are distinguishable from prostaglandins in that they are 11-deoxy compounds.

SUMMARY OF THE INVENTION

It is a purpose of this invention to provide novel phenylene prostaglandin analogs and intermediates and processes for making them.

The novel prostaglandin analogs of this invention each have a meta-substituted divalent phenylene moiety

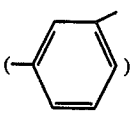

in the carboxyl-terminated side chain of the prostanoic acid structure (1). This phenylene group is in place of three of the six methylene portions of said chain.

For example, one of the novel prostaglandin analogs of this invention is represented by the formula:

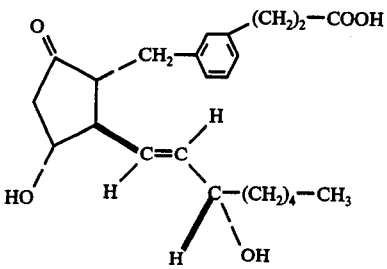

Based on its relationship to $PGE_1$ and prostanoic acid, the compound of formula V is named "4,5,6-trinor-3,7-inter-m-phenylene-$PGE_1$". This name is typical of the names used hereinafter, and is understood by reference to the structure and numbering system of prostanoic acid (formula 1 above).

The use of "trinor" in the names of the novel compounds of this invention indicates the absence of three of the chain carbon atoms and the attached hydrogen atoms. The numbers in front of "trinor" indicate which of the original prostanoic acid carbon atoms are missing in the named compound.

The numbers preceding the expression "inter-m-phenylene" indicate that m-phenylene has been inserted between the two carbon atoms so numbered in the formula of prostanoic acid.

Including among the novel inter-m-phenylene compounds of this invention are compounds represented by the formulas:

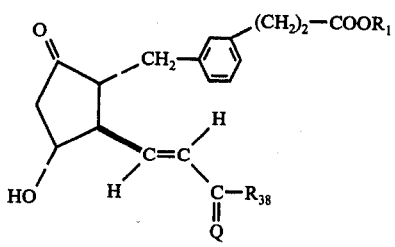

and the, mixtures of those compounds and their respective enantiomers represented by the mirror images of the above formulas.

In formula VI, Q is

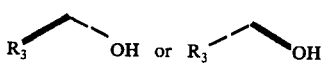

wherein $R_3$ is hydrogen or alkyl of one to 4 carbon atoms, inclusive; $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; and $R_{38}$ is (1) 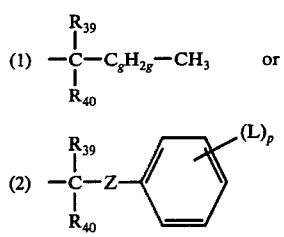 or (2) 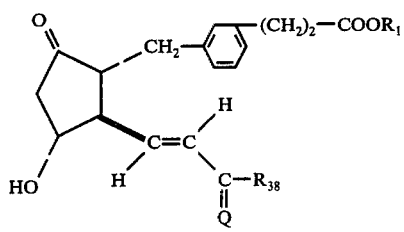

wherein $C_gH_{2g}$ is alkylene of one to 9 carbon atoms, inclusive, with one to 5 carbon atoms, inclusive, in the chain between —$CR_{39}R_{40}$— and terminal methyl, wherein $R_{39}$ and $R_{40}$ are hydrogen, alkyl of one to 4 carbon atoms, inclusive, or fluoro, being the same or different, with the proviso that one of $R_{39}$ and $R_{40}$ is fluoro only when the other is hydrogen or fluoro and the further proviso that neither $R_{39}$ nor $R_{40}$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_{39}R_{40}$— and the phenyl ring; and wherein L is alkyl of one to 4 carbon atoms, inclusive, fluoro, chloro, trifluoromethyl, or —$OR_{41}$— wherein $R_{41}$ is alkyl of one to 4 carbon atoms, inclusive, and p is zero, one, 2 or 3, with the proviso that not more than two L's are other than alkyl and when p is 2 or 3 the L's are either the same or different.

There are also included the pharmacologically acceptable salts when $R_1$ is hydrogen.

I claim:

1. An optically active compound of the formula

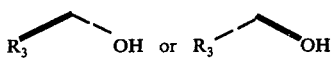

or a mixture comprising that compound and the enantiomer thereof, wherein Q is

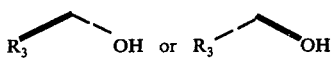

wherein $R_3$ is hydrogen or alkyl of one to 4 carbon atoms, inclusive;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; including the pharmacologically acceptable salts thereof when $R_1$ is hydrogen; wherein $R_{38}$ is (1) 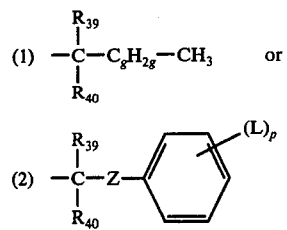 or (2) 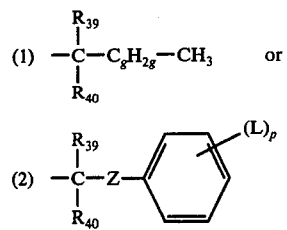

wherein $C_gH_{2g}$ is alkylene of one to 9 carbon atoms, inclusive, with one to 5 carbon atoms, inclusive, in the chain between —$CR_{39}R_{40}$— and terminal methyl, wherein $R_{39}$ and $R_{40}$ are hydrogen, alkyl of one to 4 carbon atoms, inclusive, of fluoro, being the same or different, with the proviso that one of $R_{39}$ and $R_{40}$ is fluoro only when the other is hydrogen or fluoro and the further proviso that neither $R_{39}$ nor $R_{40}$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_{39}R_{40}$— and the phenyl ring; and wherein L is alkyl of one to 4 carbon atoms, inclusive, fluoro, chloro, trifluoromethyl, or —$OR_{41}$— wherein $R_{41}$ is alkyl of one to 4 carbon atoms, inclusive, and p is zero, one, 2 or 3, with the proviso that not more than two L's are other than alkyl and when p is 2 or 3 the L's are either the same or different.

2. A compound according to claim 1 wherein $R_{38}$ is

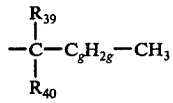

wherein $C_gH_{2g}$, $R_{39}$, and $R_{40}$ are as defined in claim 1.

3. A compound according to claim 2 wherein Q is

4. A compound according to claim 2 wherein Q is

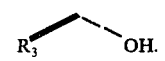

5. A compound according to claim 4 wherein the sum of the number of carbon atoms in $R_3$, $R_{39}$, and $R_{40}$ is less than 7.

6. A compound according to claim 5 wherein $C_gH_{2g}$ is alkylene of one to 5 carbon atoms, inclusive.

7. A compound according to claim 6 wherein $C_gH_{2g}$ is alkylene of 2, 3, or 4 carbon atoms and $R_{39}$ and $R_{40}$ are hydrogen, methyl, ethyl, or fluoro, being the same or different.

8. A compound according to claim 7 wherein $C_gH_{2g}$ is trimethylene.

9. A compound according to claim 8 wherein both $R_{39}$ and $R_{40}$ are hydrogen.

10. A compound according to claim 9 wherein $R_3$ is hydrogen.

11. A compound according to claim 10 wherein $R_1$ is alkyl of one to 12 carbon atoms.

12. 4,5,6-Trinor-3,7-inter-m-phenylene-PGE$_1$, methyl ester, a compound according to claim 11.

13. A compound according to claim 10 wherein $R_1$ is hydrogen or a pharmacologically acceptable cation.

14. 4,5,6-Trinor-3,7-inter-m-phenylene-$PGE_1$, a compound according to claim 13.

15. A compound according to claim 9 wherein $R_3$ is methyl.

16. A compound according to claim 8 wherein one or both of $R_{39}$ and $R_{40}$ are methyl.

17. A compound according to claim 16 wherein $R_3$ is hydrogen.

18. A compound according to claim 17 wherein $R_1$ is alkyl of one to 12 carbon atoms.

19. A compound according to claim 17 wherein $Rl_1$ is hydrogen or a pharmacologically acceptable cation.

20. 4,5,6-Trinor-3,7-inter-m-phenylene-16-methyl-$PGE_1$, a compound according to claim 19.

21. 4,5,6-Trinor-3,7-inter-m-phenylene-16,16-dimethyl$PGE_1$, a compound according to claim 19.

22. A compound according to claim 8 wherein one or both of $R_{39}$ and $R_{40}$ are fluoro.

23. A compound according to claim 22 wherein $R_3$ is hydrogen.

24. A compound according to claim 23 wherein $R_1$ is alkyl of one to 12 carbon atoms.

25. A compound according to claim 23 wherein $R_1$ is hydrogen or a pharmacologically acceptable cation.

26. 4,5,6-Trinor-3,7-inter-m-phenylene-16-fluoro$PGE_1$, a compound according to claim 25.

27. 4,5,6-Trinor-3,7-inter-m-phenylene-16,16-difluoro$PGE_1$, a compound according to claim 25.

28. A compound according to claim 1 wherein $R_{38}$ is

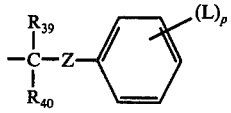

wherein L, p, $R_{39}$, $R_{40}$, and Z are as defined in claim 1.

29. A compound according to claim 28 wherein Z is oxa (—O—).

30. A compound according to claim 29 wherein Q is

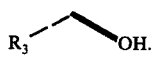

31. A compound according to claim 29 wherein Q is

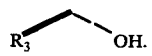

32. A compound according to claim 31 wherein $R_{39}$ and $R_{40}$ are hydrogen, methyl, or ethyl, being the same or different.

33. A compound according to claim 32 wherein both $R_{39}$ and $R_{40}$ are hydrogen.

34. A compound according to claim 33 wherein $R_3$ is hydrogen.

35. A compound according to claim 34 wherein $R_1$ is alkyl of one to 12 carbon atoms.

36. A compound according to claim 34 wherein $R_1$ is hydrogen or a pharmacologically acceptable cation.

37. 4,5,6,17,18,19,20-Heptanor-3,7-inter-m-phenylene-16-phenoxy-$PGE_1$, a compound according to claim 36.

38. 4,5,6,17,18,19,20-Heptanor-3,7-inter-m-phenylene-16(m-tolyloxy)-$PGE_1$, a compound according to claim 36.

39. 4,5,6,17,18,19,20-Heptanor-3,7-inter-m-phenylene-16-(p-tolyloxy)-$PGE_1$, a compound according to claim 36.

40. 4,5,6,17,18,19,20-Heptanor-3,7-inter-m-phenylene-16-(m-chlorophenoxy)-$PGE_1$, a compound according to claim 36.

41. 4,5,6,17,18,19,20-Heptanor-3,7-inter-m-phenylene-16-(p-chlorophexnoxy)-$PGE_1$, a compound according to claim 36.

42. 4,5,6,17,18,19,20-Heptanor-3,7-inter-m-phenylene-16-(m-fluorophenoxy)-$PGE_1$, a compound according to claim 36.

43. 4,5,6,17,18,19,20-Heptanor-3,7-inter-m-phenylene-16-(p-fluorophenoxy)-$PGE_1$, a compound according to claim 36.

44. 4,5,6,17,18,19,20-Heptanor-3,7-inter-m-phenylene-16-(m-trifluoromethylphenoxy)-$PGE_1$, a compound according to claim 36.

45. 4,5,6,17,18,19,20-Heptanor-3,7-inter-m-phenylene-16-(p-trifluoromethylphenoxy)-$PGE_1$, a compound according to claim 36.

46. 4,5,6,17,18,19,20-Heptanor-3,7-inter-m-phenylene-16-(m-anisyloxy)-$PGE_1$, a compound according to claim 36.

47. 4,5,6,17,18,19,20-Heptaonor-3,7-inter-m-phenylene-16-(p-anisyloxy)-$PGE_1$, a compound according to claim 36.

48. A compound according to claim 33 wherein $R_3$ is methyl.

49. A compound according to claim 32 wherein one or both of $R_{39}$ and $R_{40}$ are methyl.

50. A compound according to claim 49 wherein $R_3$ is hydrogen.

51. A compound according to claim 50 wherein $R_1$ is alkyl of one to 12 carbon atoms.

52. A compound according to claim 50 wherein $R_1$ is hydrogen or a pharmacologically acceptable cation.

53. 4,5,6,18,19,20-Hexanor-3,7-inter-m-phenylene-16-methyl-16-phenoxy-$PGE_1$, a compound according to claim 52.

54. A compound according to claim 28 wherein z is $C_jH_{2j}$ wherein $C_jH_{2j}$ is as defined in claim 1.

55. A compound according to claim 54 wherein Q is

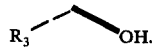

56. A compound according to claim 54 wherein Q is

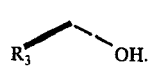

57. A compound according to claim 56 wherein $R_{39}$ and $R_{40}$ are hydrogen, methyl, ethyl, or fluoro, being the same or different.

58. A compound according to claim 57 wherein $R_{39}$ and $R_{40}$ are both hydrogen.

59. A compound according to claim 58 wherein $R_3$ is hydrogen.

60. A compound according to claim 59 wherein $C_jH_{2j}$ is a valence bond.

61. 4,5,6,17,18,19,20-Heptanor-3,7-inter-m-phenylene-16-phenyl-PGE$_1$, a compound according to claim 60.

62. A compound according to claim 59 wherein $C_jH_{2j}$ is methylene.

63. 4,5,6,18,19,20-Hexanor-3,7-inter-m-phenylene-17-phenyl-PGE$_1$, a compound according to claim 62.

64. 4,5,6,18,19,20-Hexanor-3,7-inter-m-phenylene-17-(m-tolyl)-PGE$_1$, a compound according to claim 62.

65. 4,5,6,18,19,20-Hexanor-3,7-inter-m-phenylene-17-(p-tolyl)-PGE$_1$, a compound according to claim 62.

66. 4,5,6,18,19,20-Hexanor-3,7-inter-m-phenylene-17-(m-chlorophenyl)-PGE$_1$, a compound according to claim 62.

67. 4,5,6,18,19,20-Hexanor-3,7-inter-m-phenylene-17-(p-chlorophenyl)-PGE$_1$, a compound according to claim 62.

68. 4,5,6,18,19,20-Hexanor-3,7-inter-m-phenylene-17-(m-fluorophenyl)-PGE$_1$, a compound according to claim 62.

69. 4,5,6,18,19,20-Hexanor-3,7-inter-m-phenylene-17-(p-fluorophenyl)-PGE$_1$, a compound according to claim 62.

70. 4,5,6,18,19,20-Hexanor-3,7-inter-m-phenylene-17-(m-trifluoromethylphenyl)-PGE$_1$, a compound according to claim 62.

71. 4,5,6,18,19,20-Hexanor-3,7-inter-m-phenylene-17-(p-trifluoromethylphenyl)-PGE$_1$, a compound according to claim 62.

72. 4,5,6,18,19,20-Hexanor-3,7-inter-m-phenylene-17-(m-anisyl)-PGE$_1$, a compound according to claim 62.

73. 4,5,6,18,19,20-Hexanor-3,7-inter-m-phenylene-17-(p-anisyl)-PGE$_1$, a compound according to claim 62.

74. A compound according to claim 59 wherein $C_jH_{2j}$ is ethylene.

75. A compound according to claim 58 wherein $R_3$ is methyl.

76. A compound according to claim 57 wherein one or both of $R_{39}$ and $R_{40}$ are methyl.

77. A compound according to claim 76 wherein $R_3$ is hydrogen.

78. A compound according to claim 77 wherein $C_jH_{2j}$ is a valence bond.

79. A compound according to claim 77 wherein $C_jH_{2j}$ is methylene.

80. 4,5,6,18,19,20-Hexanor-3,7-inter-m-phenylene-16-methyl-17-phenyl-PGE$_1$, a compound according to claim 79.

81. 4,5,6,18,19,20-Hexanor-3,7-inter-m-phenylene-16,16-dimethyl-17-phenyl-PGE$_1$, a compound according to claim 79.

82. A compound according to claim 77 wherein $C_jH_{2j}$ is ethylene.

83. A compound according to claim 57 wherein one or both of $R_{39}$ and $R_{40}$ are fluoro.

84. A compound according to claim 83 wherein $R_3$ is hydrogen.

85. A compound according to claim 84 wherein $C_jH_{2j}$ is a valence bond.

86. A compound according to claim 84 wherein $C_jH_{2j}$ is methylene.

87. 4,5,6,18,19,20-Hexanor-3,7-inter-m-phenylene-16-fluoro-17-phenyl-PGE$_1$, a compound according to claim 86.

88. 4,5,6,18,19,20-Hexanor-3,7-inter-m-phenylene-16,16-difluoro-17-phenyl-PGE$_1$, a compound according to claim 86.

89. 4,5,6,19,20-Pentanor-3,7-inter-m-phenylene-18-phenyl-PGE$_1$, a compound according to claim 84.

* * * * *